(12) United States Patent
Matak et al.

(10) Patent No.: US 10,293,207 B1
(45) Date of Patent: May 21, 2019

(54) ATHLETIC PERFORMANCE ESTIMATION TECHNIQUES

(71) Applicant: Mayfonk Athletic LLC, Ft. Lauderdale, FL (US)

(72) Inventors: Martin T. Matak, Plantation, FL (US); Jonathan Mitts, Ft. Lauderdale, FL (US); Jef Spaleta, Fairbanks, AK (US)

(73) Assignee: Mayfonk Athletic LLC, Ft. Lauderdale, FL (US)

( * ) Notice: Subject to any disclaimer, the term of this patent is extended or adjusted under 35 U.S.C. 154(b) by 108 days.

(21) Appl. No.: 15/396,907

(22) Filed: Jan. 3, 2017

Related U.S. Application Data

(60) Provisional application No. 62/274,120, filed on Dec. 31, 2015.

(51) Int. Cl.
    *A63B 24/00*  (2006.01)
    *A41D 1/00*  (2018.01)
    (Continued)

(52) U.S. Cl.
    CPC .......... *A63B 24/0006* (2013.01); *A41D 1/002* (2013.01); *A63B 24/0062* (2013.01); *A63B 69/00* (2013.01); *A63B 71/0622* (2013.01); *G09B 19/0038* (2013.01); *A63B 2024/0012* (2013.01); *A63B 2220/12* (2013.01); *A63B 2220/20* (2013.01); *A63B 2220/30* (2013.01); *A63B 2220/40* (2013.01); *A63B 2220/53* (2013.01); *A63B 2220/56* (2013.01); *A63B 2220/62* (2013.01); *A63B 2220/802* (2013.01); *A63B 2220/803* (2013.01); *A63B 2220/805* (2013.01); *A63B 2220/836* (2013.01); *A63B 2225/50* (2013.01); *A63B 2230/06* (2013.01); *A63B 2230/50* (2013.01)

(58) Field of Classification Search
    None
    See application file for complete search history.

(56) References Cited

U.S. PATENT DOCUMENTS

2007/0208544 A1* 9/2007 Kulach ................. A61B 5/1112
                                                    702/189
2009/0319221 A1* 12/2009 Kahn ................... A61B 5/1123
                                                    702/141
(Continued)

*Primary Examiner* — Jason T Yen
(74) *Attorney, Agent, or Firm* — Duane Morris LLP

(57) ABSTRACT

Systems and methods are described for computing real-time athletic performance parameters that characterize an athlete's activity while participating in a sport. A system includes a performance measuring unit that is, for example, attached to an article of clothing of an athlete and that monitors movement and activity while the athlete participates in the sport. The performance measuring unit can include multiple types of activity-based sensors (e.g., an accelerometer, a magnetometer, and/or a gyroscope) that are configured to collect sensor data reflective of positional changes of the performance measuring unit. The computing unit of the performance measuring unit processes the collected sensor data in real-time using specified techniques to identify the occurrence of "events," which refer to a particular time periods during which the collected sensor data are associated with movements of interest (e.g., movements associated with a high intensity action).

20 Claims, 6 Drawing Sheets

(51) Int. Cl.
   *A63B 69/00* (2006.01)
   *G09B 19/00* (2006.01)
   *A63B 71/06* (2006.01)

(56) References Cited

U.S. PATENT DOCUMENTS

| | | | |
|---|---|---|---|
| 2010/0144414 A1* | 6/2010 | Edis | A63B 24/0006 463/8 |
| 2015/0106052 A1* | 4/2015 | Balakrishnan | A61B 5/1123 702/150 |
| 2015/0153374 A1* | 6/2015 | Balakrishnan | G01P 13/00 702/178 |
| 2016/0073961 A1* | 3/2016 | Soh | G06F 19/3481 600/595 |

\* cited by examiner

ATHLETIC PERFORMANCE ESTIMATION TECHNIQUES

CROSS-REFERENCE TO RELATED APPLICATIONS

This application claims priority to U.S. Application Ser. No. 62/274,120, filed on Dec. 31, 2015, which is incorporated by reference herein in its entirety.

FIELD

The present specification is related generally to wearable devices having sensors for measuring and transmitting information.

BACKGROUND

Conventional athletic wear such as shoes and boots can include technology for measuring and monitoring specific aspects of athletic performance of an individual. For example, pedometers can be incorporated in footwear for measuring a distance that a person walks or runs based upon body motion of the person. In addition, other types of athletic wear can be designed to measure and display specific physiological parameters such as pulse rate, weight, and calorie expenditure.

SUMMARY

In general, this specification describes systems and methods relating to computing real-time athletic performance parameters that characterize an athlete's activity while participating in a sport. A system includes a performance measuring unit that is, for example, attached to an article of clothing of an athlete and that monitors movement and activity while the athlete participates in the sport. The performance measuring unit can include multiple types of activity-based sensors (e.g., an accelerometer, a magnetometer, and/or a gyroscope) that are configured to collect sensor data reflective of positional changes of the performance measuring unit.

The computing unit of the performance measuring unit processes the collected sensor data in real-time using specified techniques to identify the occurrence of "events," which refer to a particular time periods during which the collected sensor data are associated with movements of interest (e.g., movements associated with a high intensity action). In this regard, the computing unit can automatically discriminate between collected sensor data indicating regular activity associated with the sport and collected sensor data indicating high-impact and/or high priority activity that relates to athletic performance.

The system is also capable of processing the collected data to perform various real-time athletic performance monitoring operations. The computing unit of the performance measuring unit may compute performance evaluation metrics based on processing the collected data, and then track the computed performance evaluation metrics in relation to particular activities performed in relation to the sport. As an example, the computing unit may derive the amount of energy exerted by an athlete while performing a specified action. The computing unit can then periodically monitor the amount of energy exerted for different actions in order to determine whether the athlete is efficiently performing the specified action.

In some implementations, the system is capable of using statistical techniques to make inferences and/or predictions relating to athletic activity. For example, the computing unit of the performance measuring unit may correlate the average amount of energy exerted by an athlete to perform a particular action and the predicted number of times that particular action is performed over a period of time in order to estimate the total physical stress imposed on the athlete. Such real-time monitoring techniques can be used to perform various types of performance assessments of athletic activity.

In one general aspect, a computer-implemented method may include: obtaining, from a plurality of sensors, data indicating samples of motion data of a user; computing a respective total acceleration value for each of the samples of motion data; determining that a total acceleration value for a particular sample from among the samples of motion data satisfies a predetermined threshold; in response to determining that the total acceleration value for the particular sample satisfies the predetermined threshold, identifying a group that includes samples of motion data that (i) are collected after the particular sample, and (ii) are determined to have a particular total acceleration value that satisfies the predetermined threshold; generating an instruction to a computing device to (i) compute, for the identified group, one or more aggregate parameters based on the samples of motion data that are included within the identified group, and (ii) compute one or more athletic parameters for the user based at least on the one or more computed aggregate parameters; and providing the instruction for output to the computing device.

Other implementations of these aspects include corresponding systems, apparatus and computer programs, configured to perform the actions of the methods, encoded on computer storage devices.

One or more implementations may include the following optional features. For instance, in some implementations, the plurality of sensors includes at least an accelerometer, a gyroscope, and a magnetometer.

In some implementations, each sample of motion data includes, for each respective coordinate axis, a measured acceleration, a measured magnetic field direction, and a measured angular velocity.

In some implementations, computing a total acceleration value for a sample of motion data includes combining an acceleration measured by the accelerometer, a magnetic field direction measured by the gyroscope, and an angular velocity measured by the magnetometer.

In some implementations, at least one of the aggregate parameters includes a value of a highest measured total acceleration that is selected from among the measured total accelerations for the samples of motion data included within the identified group.

In some implementations, the one or more athletic performance parameters include a predicted amount of kinetic energy expended by the user during a time period associated with the identified group.

In some implementations, the one or more athletic performance parameters include a predicted physical impact of the detected motion on the user during a time period associated with the identified group.

The details of one or more implementations are set forth in the accompanying drawings and the description below. Other potential features and advantages will become apparent from the description, the drawings, and the claims.

BRIEF DESCRIPTION OF THE DRAWINGS

In the drawings, like reference numbers represent corresponding parts throughout.

DETAILED DESCRIPTION

Figure 1A:
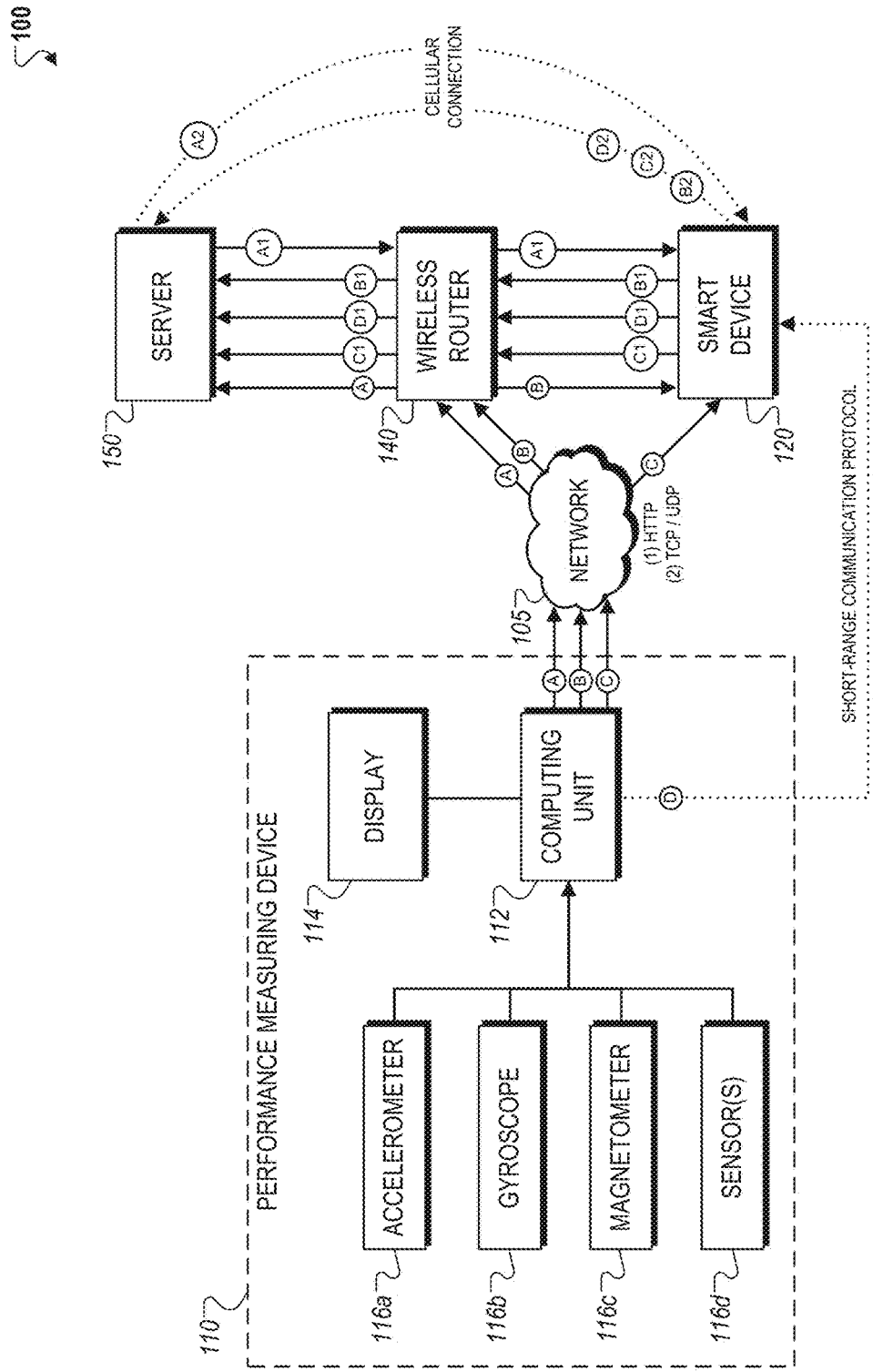
FIG. 1A is a block diagram that illustrates an example of a performance measurement system.

In general, this specification describes systems and methods relating to computing real-time athletic performance parameters that characterize an athlete's activity while participating in a sport. A system includes a performance measuring unit that is attached to, for example, an article of clothing of the athlete and that monitors movement and activity while the athlete participates in the sport.

As described throughout, "sensor data" refers to any type of raw data measured and/or collected by sensors associated with a performance measuring unit. Examples of sensor data can include accelerometer data, gyroscope data, magnetometer data, or other types of activity-based or movement-based data.

As described throughout, an "event" refers to a specified time period during which one or more types of sensor data satisfies a predetermined threshold. For example, an event refers to a time period during which a measured total acceleration (e.g., a combined magnitude of acceleration along all coordinate axis) exceeds a specified threshold value. As described below, in this example, the system identifies a starting time point for an event when an instantaneous measured total acceleration for a collected sensor data sample exceeds the specified threshold value. The system then identifies the ending time point for the event when an instantaneous measured total acceleration for a subsequently collected sensor data sample falls below the specified threshold value.

As described throughout, an "athletic performance parameter" refers to a computed metric that is descriptive of an athlete's physical activity. One example of athletic performance parameters includes peak acceleration, which refers to the highest magnitude of instantaneous acceleration measured during an event. As described below, peak acceleration strongly correlates with the amount of exertion and/or stress associated with an event. Another example of an athletic performance parameter is "surge" (or "jerk"), which refers to the rate of change in instantaneous acceleration during an event. Other examples are described in more detail below.

As described throughout, "real-time data" refers information that is collected and/or processed instantaneously with minimal delay after the occurrence of a specified event, condition, or trigger. For instance, "real-time sensor data" or "real-time athletic performance parameters" refer to motion data (e.g., measured acceleration, direction of movement, etc.) that is processed with minimal delay after an athlete performs a physical activity that is sensed by motion sensors (e.g., accelerometers, gyroscopes, magnetometers). The minimal delay in collecting and processing the real-time motion data is based on a sampling rate of the athletic performance device that senses an athlete's physical activity, and a time delay associated with processing collected sensor data. As an example, the athletic performance device may collect 10 samples of sensor data every 100 milliseconds (with a "sample" being comprised of values for all three axes for each of the sensors in question).

As described throughout, "angle change" (or "cuts") refers to a rapid change in the direction of momentum, whether resulting from self-powered movement, or resulting from impact with another physical object. For instance, acceleration can be measured in component directions (e.g., x-axis, y-axis, and z-axis) and the magnitudes of component accelerations can be monitored to determine changes in angle. Angle change determinations can be used to assess athleticism, predict movement and/or analyze how changes in angle impact the measurements of other athletic performance parameters. In addition, baselines can be established for peak performance as well as re-injury protocols and return to play protocols. Multi-appendage assessments can be developed and established using angle change results for comparisons to benchmark historical data as well as real-time appendage to appendage analysis.

FIG. 1A is a block diagram that illustrates an example of a system 100 that is capable of transmitting athletic performance data. The system 100 can include an athletic performance unit 110, a smart device 120, a wireless router 140, and a server 150. The performance measuring device 110 further includes an accelerometer 116a, a gyroscope 116b, a magnetometer 116c, sensors 116d, a computing unit 112, and a display 114. In some implementations, the performance measuring device 110 may include less than all of the sensors or components depicted in FIG. 1A. For example, in some implementations, the performance measuring device 110 only includes an accelerometer 116a. In addition, in some implementations, the display 114 is an optional component of the performance measuring device 110.

In general, the architecture of the system 100 enables the transmission of athletic performance data collected by the performance measuring device 110 (e.g., measured acceleration) to either the smart device 120 and/or the server 150. As illustrated, the system 100 enables various alternative transmission pathways for the collected data based on the configuration of the system and the wireless communication protocol used to transmit the collected data.

The performance measuring device 110 generally transmits collected sensor data to the smart device 120 and/or the server 150 using various alternative transmission pathways. The transmission pathways vary based on the type of communication protocol used to transmit the collected sensor data and the sequence of components used to transmit the collected sensor data to the server 150. Once the collected sensor data is transmitted to the server 150, the system 100 can broadcast the athletic performance data to remote devices.

In the figure, alternative transmission pathways are represented by letters, "A," "B," "C," and "D." In addition, alternative sub-pathways are represented by numbers following letters for alternative pathways (e.g., "C1" and "C2" represent alternative sub-pathways for the transmission pathway represented by the letter "C").

In the transmission pathway represented by "A," the performance measuring device 110 transmits the collected sensor data to the server 150 through the wireless router 140 without routing the collected data through the smart device 120. In this transmission pathway, because the smart device 120 does not initially obtain the collected sensor data, the server 150 transmits the obtained sensor data either through the wireless router 140 (e.g., sub-pathway "A1") or through a cellular connection (e.g., sub-pathway "A2").

In the second transmission pathway represented by "B," the performance measuring device 110 transmits the collected sensor data to the smart device 120 through the wireless router 140 (e.g., using TCP or UDP), and then the smart device 120 relays the obtained data to the server 150. For example, the smart device 120 can transmit the obtained data to the server 150 through the wireless router 140 (e.g., sub-pathway "B1") or through a cellular connection (e.g., sub-pathway "B2").

In the third transmission pathway represented by "C," the performance measuring device 110 transmits the collected sensor data to the smart device 120 directly to the smart device 120 (e.g., using TCP or UDP over WiFi Direct), and then the smart device 120 relays the obtained data to the server 150. For example, the smart device 120 can transmit the obtained data to the server 150 through the wireless router 140 (e.g., sub-pathway "C1") or through a cellular connection (e.g., sub-pathway "C2"). In this transmission pathway, the wireless router 140 is not needed to transmit the collected sensor data from the computing unit 112 to the smart device 120.

In the fourth transmission pathway represented by "D," the performance measuring device 110 transmits the collected sensor data to the smart device 120 directly to the smart device using a short-range communication protocol (e.g., Bluetooth, NFC, IR, etc.) that does not require network connectivity. The smart device 120 then relays the obtained data to the server 150. For example, the smart device 120 can transmit the obtained data to the server 150 through the wireless router 140 (e.g., sub-pathway "D1") or through a cellular connection (e.g., sub-pathway "D2").

As described above, the performance measuring device 110 can be integrated within or placed on one or more articles of clothing such as shoes, gloves, wrist bands, belts, straps, hats, shorts, caps, shirts, sports bras, underwear, helmets, pads, pants, compression sleeves, compression socks and half socks, shoulder pads, protective pads or other similar types of clothing.

The performance measurement unit 110 includes a computing unit 112 that can communicate over an interface with sensor units such as the accelerometer 116a, the gyroscope 116b, the magnetometer 116c, and the one or more sensors 116d. The computing unit 112 can be a controller, a microcontroller, or any other type of processor. The computing device 112 can include short-term memory and/or long-term persistent (non-volatile) storage for temporarily storing data exchanged with the sensor units, and/or storing computer-implemented instructions that control the operations of the sensor units. In some implementations, the computing unit 112 additionally includes an antenna that transmits some form of electromagnetic radiation to devices that are electrically or communicatively coupled to the performance measurement unit 110.

The computing unit 112 exchanges performance data with the accelerometer 116a, the gyroscope 116b, the magnetometer 116c, and the one or more sensors 116d. For example, the computing unit 112 may exchange data transmissions using an interface that can include, for example, a serial, parallel, Bluetooth, USB, or other types of generic bus that are capable of transmitting information collected by the accelerometer 116a, the gyroscope 116b, the magnetometer 116c, and the one or more sensors 116d. Although not depicted in FIG. 1A, the computing unit 112 can exchange performance data with other types of sensor units such as an ultra-wideband transceiver, an ultrasonic sensor, an infrared sensor, a global positioning system (GPS), a pressure sensor, a piezo element, and/or optical light sensors.

The accelerometer 116a, the gyroscope 116b, the magnetometer 116c, and the one or more sensors 116d can be used to measure one or more athletic performance parameters. For example, the one or more athletic performance parameters can include, but are not limited to, acceleration, jerk (the derivative of acceleration, also known as surge), cadence, distance, GPS location, vertical leap, vertical touch height, heart rate, pace, pressure, power, stress, kinetic energy, contact, speed, swing plane, and/or ambient body temperature.

Once the accelerometer 116a, the gyroscope 116b, the magnetometer 116c, and the one or more sensors 116d measure one or more athletic performance parameters, the measured athletic performance parameters can be transmitted to the computing device 112. The computing device 112 can process the performance data in real-time to obtain a set of desired athletic performance data. For example, the computing device 112 can obtain performance data such as a maximum jump height, a maximum vertical touch height, an average jump height for a particular individual, and/or the number of jumps made by a particular individual within a predetermined time interval. In addition, the computing device 112 can be configured to provide period data for particular time intervals. The performance data can then be transferred to the smart device 120 over the network 105.

The performance measurement unit 110 also includes a display unit 114 that provides an output of the performance data measured by the accelerometer 116a, the gyroscope 116b, the magnetometer 116c, and the one or more sensors 116d, and processed by the computing unit 112. For instance, the display unit 114 can provide outputs of the values associated with the one or more athletic parameters, visualizations indicative of athletic trends indicated by the one or more parameters over a period of time, or other types of related information associated with the measured performance data. In other implementations, the performance measurement unit 110 does not include a display unit 114. In these implementations, visualization of data may be provided via an external display unit communicatively coupled to the performance measurement unit 110 through, for example, network 105. The external display unit may, for example, be integrated into the smart device 120.

The smart device 120 can be any type of electronic computing device with network connectivity. For example, the smart device 120 can be a smart phone, a tablet computing device, a smart watch, smart apparel, smart glasses, smart lenses, a laptop computing device, a desktop computing device. For instance, the athletic performance data measured by the performance measuring device 110 can be transmitted to a personal computer of an athlete to track individual training progress, and/or provide information related to performance improvements. Alternatively, in other instances, the smart device 120 can be a non-personal computing device such as a web server or a network computer. For example, athletic performance data during a sporting event can be detected by the athletic performance unit 110 and transmitted to a server in order to display the measured athletic performance data on a television broadcast of the sporting event.

Data collected by the sensors includes acceleration data, gyroscope data, and magnetometer data. Acceleration data includes a measured horizontal and/or a measured vertical acceleration, for instance, measured in terms of gravitational force (g-forces), associated with an individual's movement over a particular period of time. For instance, the magnitude of measured acceleration can be used to indicate an intensity or an impact associated with a particular physical action by the individual. In this regard, measurement of acceleration can be used to quantify force exerted by an individual, the energy exerted during a movement, the power generated during a movement, and/or potential physical impacts.

The acceleration data can be used for a variety of performance monitoring purposes. In one example, the acceleration and impact data can be used for real-time automotive analysis for injury prevention. In this example, the magnitude of acceleration can be used to determine the amount of force exerted by an individual and predict a risk of injury based on the amount of force exerted during a particular physical activity. In another example, acceleration data can be used with existing devices such as a head and neck support (HANS) device to assist drivers and/or medical personnel in making decisions during an accident. In this example, the magnitude of impact can be used to predict actions that should be taken to prevent additional injury and/or provide treatment for existing injuries. In another example, acceleration data can be used to determine when an individual has fallen and/or predict the likelihood of a fall.

In other instances, the acceleration data can be used to provide quantitative assessments of actions taken by athletes during a sporting event. For example, an acceleration measurement can be used to determine an intensity associated with actions taken by an athlete during a sporting event. This can include intensity measurements made when a runner pushes off the starting block during track and field races, or when a curler delivers a rock. In other example, acceleration measurement can be used to determine an impact with surrounding physical objects. This can include impact measurements that indicate a water surface impact when a diver comes into contact with water during a dive. It can also include an example of the intensity a basketball player has when jump or making cuts. Other instances can include utilizing impact measurements to determine efficiency of actions taken.

In other instances, the acceleration data can be used to provide visualizations and/or other graphical displays associated with an individual's movement. For example, acceleration measurement can be used to depict real-time speed of objects that come into contact with appendages. In this example, visible indicators can be superimposed on action replays to depict magnitudes of speed to enhance user experience. The visualizations may be presented on a display of the smart device 120, the display 114 of the performance unit 110, and/or an external display distinct from but communicatively coupled to the performance unit 110 and/or the smart device 120 over the network 105.

Examples of acceleration measurements can include peak accelerations, surge, and angle change. Although these examples are described in detail below, other types of measurements can be possible.

The hundreds or thousands of such peak accelerations that occur over a typical workout or athletic performance can also be used to determine the amount of physical exertion and stress. For example, many large magnitude peak accelerations occurring over a sufficiently long time may indicate that an individual may have exerted physical force for a sustained period of time, increasing the risk of injury. In such instances, peak accelerations can be depicted graphically on a line graph as a function of time or a histogram graph to indicate the frequency of force exertions at various magnitudes. In each of these examples, a set of statistical values such as counts, averages, or sums may be determined based on peak acceleration data in order to make determinations related to physical exertion and stress.

In some instances, surge measurements can be used in athletic training exercises to determine the effectiveness of an individual's technique. For example, self-powered high surge events which can be referred to as "positive" high surge events (e.g., a basketball dunk, a race start, etc.), can be monitored to determine how effective an individual is at generating rapid acceleration increases on demand. In this regard, surge measurements can be used to set training goals for individuals based on correlating other types of athletic performance parameters (e.g., vertical height) with physical impact on human body. Another example can be a "negative" high surge event in which an athlete is performing a high surge event such as landing and does so with an inappropriate movement indicating a high surge measurement with a "negative high surge classification (the athlete landed poorly causing a negative high surge or stress surge).

In some instances, surge measurements can be used to classify certain types of physical activities within a training regimen based on distinguishing between high surge and low surge activities. For example, low surge activities can be included within a training regimen when an individual is recovering from surgery and/or has experienced an injury that makes him/her susceptible to physical injury. In addition, surge measurements can also be used to evaluate whether the individual's athletic ability is recovering in line with the individual's physical condition.

Figure 1B:
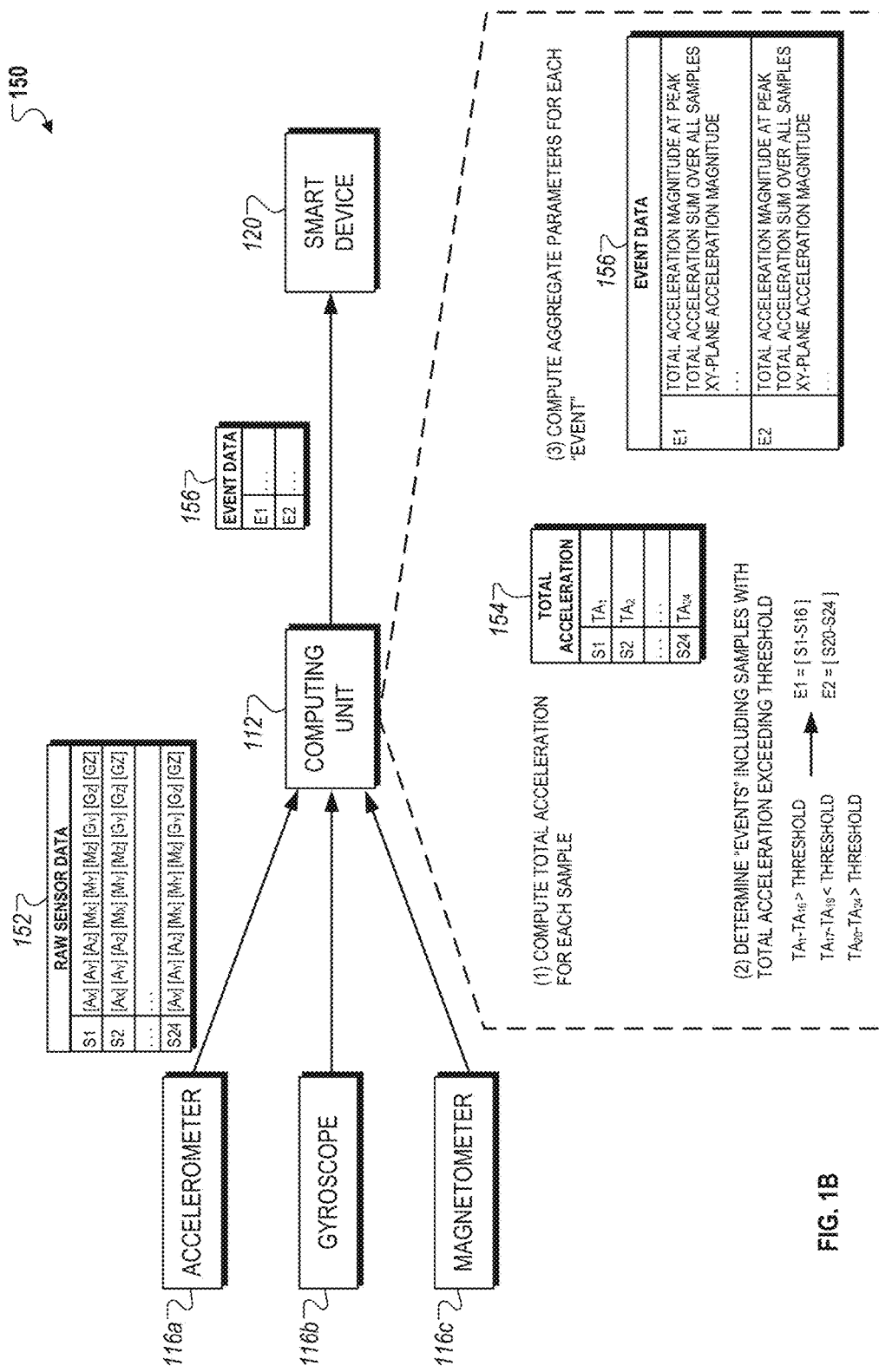
FIG. 1B is a conceptual diagram that illustrates an example of a system that is capable of computing real-time athletic performance parameters.

FIG. 1B is a conceptual diagram that illustrates an example of a system 150 that is capable of computing real-time athletic performance parameters. The system 150 generally obtains sensor data collected by the accelerometer 116*a*, the gyroscope 116*b*, and the magnetometer 116*c*, processes the obtained sensor data to identify the occurrence of an event as described above, and in response to detecting the occurrence of an event, computes one or more athletic performance parameters that characterizes detected physical activity during a time period associated with the event. In some instances, the systems 150 and 100 illustrated in FIGS. 1A and 1B are components of the same device (e.g., the performance measuring unit 110).

In more detail, the computing device 112 of the performance measuring unit 110 illustrated in FIG. 1A initially obtains raw sensor data 152 from the accelerometer 116*a*, the gyroscope 116*b*, and the magnetometer 116*c*. The raw sensor data 152 includes sensor measurements that are collected as "samples," within the obtained data. The number of samples that are included within a single data transmission obtained by the computing unit 112 is dependent on its sampling rate. In the implementation illustrated, the computing unit 112 collects 10 samples of sensor data every 100 milliseconds.

Each sample of sensor data can include, for example, nine individual sensor measurements. For instance, the sensor measurements $A_X$, $A_Y$, and $A_Z$ refer to respective acceleration measurements along the x, y, and z coordinate axis measured by the accelerometer 116*a*. The acceleration measurements are in terms of gravitational force (G) and can have an effective range between, for example, +/−16 G. The sensor measurements $G_X$, $G_Y$, and $G_Z$ refer to respective angular adjustments along the x, y, and z coordinate axis measured by the gyroscope 116*b*. The angular measurements are measured in degrees per second and can have an effective range between, for example, +/−2000 degrees per second. The sensor measurements $M_X$, $M_Y$, and $M_Z$ refer to respective magnetic field strength along the x, y, and z coordinate axis measured by the magnetometer 116*c*. The magnetic field measurements are measured in Gauss and can have an effective range between, for example, +/−16 Gauss.

In the example illustrated, each collected sensor data transmission to the computing unit 112 includes 24 samples that each include nine sensor measurements. Each group of sensor measurements within a sample is associated with a sample identifier, which then enables the computing unit 112 to identify a time point associated with each sensor measurement. For example, sensor measurements within the sample "S1" are collected prior to the sensor measurements within the sample "S24." Therefore, the computing unit 112, when processing the sensor measurements within the raw sensor data 152, iteratively processes the sensor measurements on a sample-by-sample basis (e.g., processing sensor measurements in sample "S1" first, followed by sensor measurements in sample "S2," and so on). As described throughout, the computing unit 112 processes the sensor measurements on the fly as sensor data is collected in real-time in order to enable real-time processing capabilities described throughout.

To process the obtained raw sensor data 152, the computing unit 112 initially computes a total acceleration value for each sample within the raw sensor data 152. As described above, a total acceleration refers to an aggregate magnitude of instantaneous acceleration measured by the accelerometer 116a. As an example, the total acceleration may be computed by using the Pythagorean theorem in three dimensions to combine the sensor measurements $A_X$, $A_Y$, and $A_Z$ measurements based on the sensor coordinate system and the relationship between each coordinate axis. In some implementations, the computed total acceleration values for each sample are stored in a table 154. Alternatively, in other implementations, the computed total acceleration values for each sample are discarded once they are determined not to satisfy the specified threshold to determine the occurrence of an event as described above.

After computing the total acceleration for each sample, the computing unit 112 then compares the computed total acceleration to a specified threshold. If a sample is determined to have a total acceleration that exceeds the threshold, the computing unit 112 considers an event to be in progress. No distinction is made between whether the event has already been in progress or has just started. Instead, accumulated statistics are simply cleared at the conclusion of any event or potential event. For example, as described in relation to FIG. 2 below, in some instances, the computing unit 112 may use an event flag to indicate if an event is in progress or not. In some implementations, the specified threshold may be set to 1.5 Gs. In other implementations, the specified threshold may be adjusted based on various factors, such as, for example, based on prior acceleration measurements for a particular athlete while performing specified actions, the type of activity and/or sport.

In the example depicted in FIG. 1B, the computing device 112 flags an event as in progress if it determines that the total acceleration $T_{A1}$ for the current sample $S_1$ exceeds the threshold. In addition, the computing device 112 terminates the first event at the sample $S_{16}$ because it determines that the total acceleration $T_{A17}$ for the sample $S_{17}$ does not exceed the specified threshold. The computing event then determines the start of a second event at the sample $S_{20}$ because its total acceleration $T_{A20}$ exceeds the specified threshold. The occurrence of the second event extends to sample $S_{24}$. Therefore, of the twenty-four samples within the raw sensor data 152, the computing device 112 determines the occurrence of two events, a first event from $S_1$ to $S_{16}$ and a second event $S_{20}$ to $S_{24}$.

In some instances, a detected occurrence of an event may extend between multiple individual data transmissions between the sensors and the computing unit 112. For instance, the second event illustrated in FIG. 1B, may extend to samples included within a second raw data transmission to the computing unit 112. In such instances, the computing unit 112 may combine the sensor measurements from the different data transmissions that correspond to a single event in order to perform the calculation of the real-time athletic performance parameters discussed in greater detail below.

Once the computing device 112 has identified an event, the computing unit 112 may aggregate sensor measurements from all samples that are determined to be included in the event. For example, for the first event in FIG. 1B, the computing unit 112 may aggregate sensor measurements from samples $S_1$ to $S_{16}$, and for the second event, the computing unit 112 may aggregate sensor measurements from $S_{20}$ to $S_{24}$.

The computing unit 112 will have calculated various aggregate parameters that characterize an athlete's physical activity over a time period associated with the event. As described below, the aggregate parameters can also be used to compute athletic parameters and or other derivative performance indicators. Examples of the aggregate parameters can include:

Total magnitude of acceleration at peak acceleration during the event

X-axis acceleration at peak of the magnitude of X-Y plane acceleration

Y-axis acceleration at peak of the magnitude of X-Y plane acceleration

Z-axis acceleration at peak of absolute value of z-axis acceleration

Total acceleration magnitude sum over all samples in event

X-axis acceleration sum over all samples in event

Y-axis acceleration sum over all samples in event

Z-axis acceleration sum over all samples in event

XY-plane acceleration magnitude sum over all samples in the event

Number of samples included in the event

Sample identifier of the sample corresponding to the peak total acceleration magnitude Sample identifier of the sample corresponding to the peak X-axis acceleration of the X-Y plane acceleration Sample identifier of the sample corresponding to the peak Y-axis acceleration of the X-Y plan acceleration Sample identifier of the sample corresponding to the peak absolute value of z-axis acceleration X-axis acceleration at the peak of the total acceleration magnitude Y-axis acceleration at the peak of the total acceleration magnitude Z-axis acceleration at the peak of the total acceleration magnitude High-precision timestamp for the start of each event High-precision timestamp for the end of each event The computing unit 112 transmits event data 156 including the calculated aggregate parameters for each event to the smart device 120. In some instances, the event data 156 may be post-processed (e.g., compressed, packaged, etc.) to improve the speed or quality of the data transmission including the event data 156 from the computing unit 112 to the smart device 120.

The smart device 120, a web server, or other receiving device may then use the aggregate parameters included within event data 156 to compute additional real-time athletic performance parameters. Descriptions of examples of athletic performance parameters, and their computations by the smart device 120, are provided below with respect to FIG. 4.

In summary, the example depicted in FIG. 1B illustrates how each individual sample represents a subset of motion data of an athlete. Each individual sample that is collected may be identified within a particular sequence, which designates the order in the sensors collected sensor data included within each sample. The total acceleration value is computed for each sample and then compared to a predetermined threshold. Consecutive samples within a sequence that have a total acceleration value that satisfied a predetermined threshold are identified and categorized in a "group" of samples that correspond to a detected event as described above. Aggregate parameters are updated for each sample included within the group of samples.

Although FIG. 1B illustrates the transmission of the event data 156 from the computing unit 112 to the smart device 120, in some implementations, the computing unit 112 or other local components of the performance measuring unit 110 may locally compute the real-time athletic performance parameters. In this regard, the event data 156 may be stored locally on memory and used to compute the real-time athletic performance parameters. The computed real-time athletic performance parameters (instead of the aggregate event parameters) are then transmitted to the smart device 120.

Figure 2:
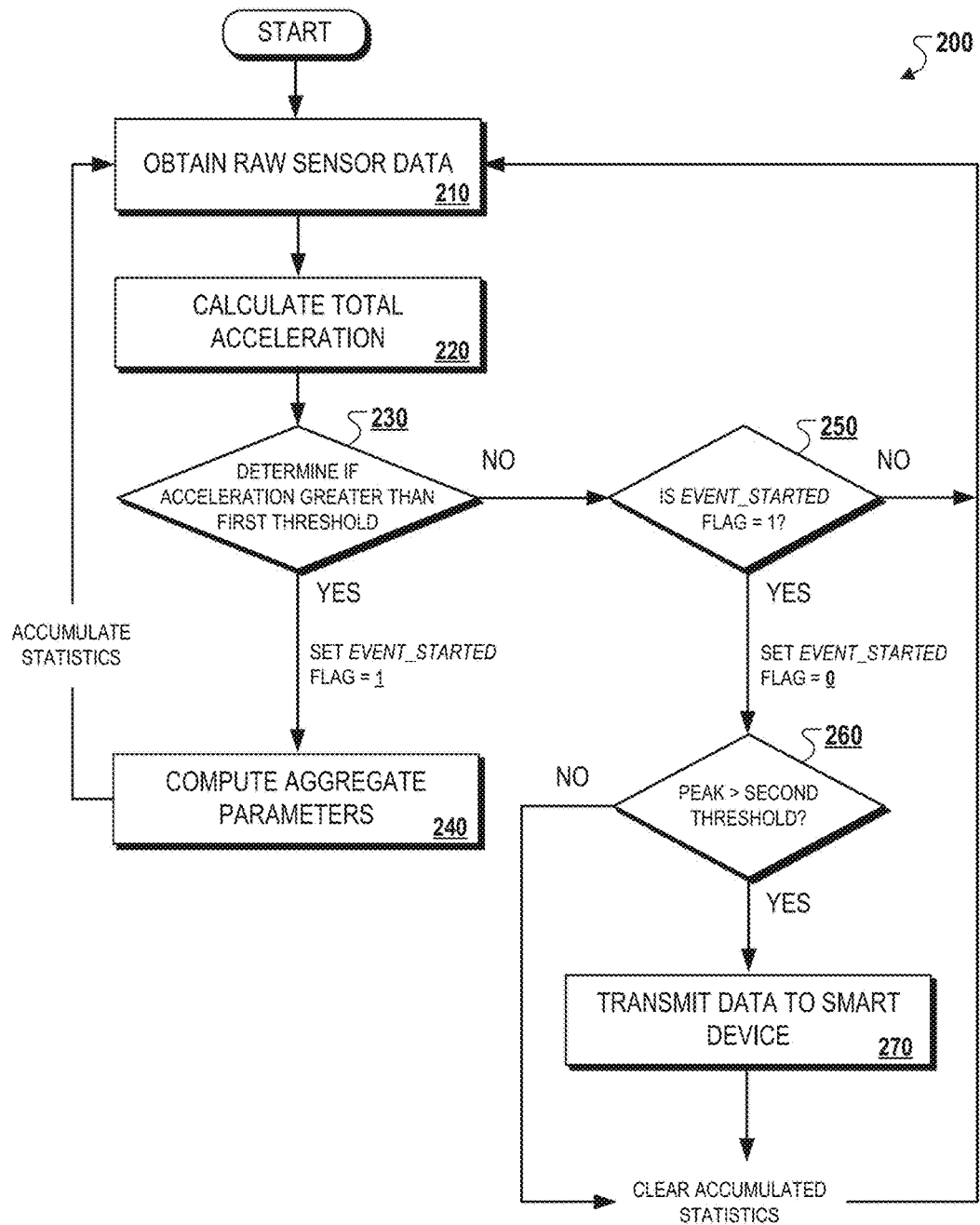
FIG. 2 is a block diagram that illustrates an example of a process for computing aggregate parameters for a detected event.

FIG. 2 is a block diagram that illustrates an example of a process 200 for computing aggregate parameters for a detected event. In general, the process 200 can be performed by, for example, the computing unit 112 illustrated in FIG. 1A. For example, the computing unit 112 can execute process 200 to determine the occurrence of an event, and computing a set of aggregate statistics for the detected event as depicted in FIG. 1B. The process 200 is performed on a sample-by-sample basis but the descriptions below are in reference to a single sample for simplicity.

Briefly, the process 200 initially includes obtaining raw sensor data (210), calculating a total acceleration (220), and determining if the calculated total acceleration is greater than a predetermined threshold value defined as signifying that an event has started (230). If value of the calculated total acceleration is greater than the predetermined threshold value, the process 200 includes computing a set of aggregate parameters related to athletic performance (240). If the value of the measured total acceleration is less than the predetermined threshold value, then the process 200 further includes checking a value of an event flag (250), determining if a peak total acceleration value is greater than a second threshold value (260), and transmitting data to a smart device based on determining if the peak total acceleration value is greater than the second threshold value (270).

In general, the computing unit 112 executes the process 200 by performing two general comparisons—comparing a calculated total acceleration to a first threshold, and comparing a peak total acceleration to a second threshold. The computing unit 112 uses the comparison to the first threshold to determine the occurrence (e.g., a starting point) of an event as described above. The computing unit 112 uses the comparison to the second threshold to discriminate between ordinary events (e.g., events that are not indicative of athletic performance of interest) and events of interest (e.g., events that correlate with significant physical activity). For example, the comparison to the second threshold can be used to discriminate between events that are detected due to noise and events that are detected due to an athlete's physical activity.

In addition, although not depicted the FIG. 2, the computing unit 112 may also perform a third type of comparison with a secondary threshold that is lower than the first threshold that is used to determine the occurrence of an event. The secondary threshold can be used to identify samples that precede a starting point of a detected event (e.g., samples that are collected prior to samples that are included in an event). The secondary threshold can also be used to identify samples that follow an ending point of the detected event (e.g., samples that are collected after samples that are included in an event). In this regard, the secondary threshold can be used to identify samples that have total acceleration values that do not satisfy the threshold value to determine the occurrence of an event but are within a certain relevant reporting range defined by the value of the secondary threshold. Both the first threshold and the secondary threshold may be adjustable based on the particular activity performed by an individual as well as physical characteristics (e.g., age, gender, physical features, etc.) associated with the individual.

Referring now the steps performed, the computing unit 112 initially obtains sensor data (210). As described above in FIG. 1B, the computing unit 112 may obtain the raw sensor data 152 collected by the accelerometer 116a, the gyroscope 116b, and the magnetometer 116c. The raw sensor data 152 includes multiple samples (e.g., $S_1$ to $S_{24}$ depicted in FIG. 1B) that each include measured sensor data along a coordinate axis.

In some implementations, the raw sensor data that is obtained by the computing unit 112 to calculate athletic performance data is primarily generated by the accelerometer 116a. In such implementations, each of the acceleration measurements described above, such as total acceleration, peak acceleration, surge, and angle change can be calculated based on data received from the accelerometer 116a without any additional data received from the gyroscope 116b, the magnetometer 116c, and the one or more sensors 116d.

The computing unit 112 then calculates a total acceleration for each sample (220). As described above, total acceleration is calculated based on aggregating the magnitudes of acceleration measured along each coordinate axis (e.g., $A_X$, $A_Y$, and $A_Z$ as illustrated in FIG. 1B).

The computing unit 112 then determines if the value of the calculated total acceleration for each sample is greater than the value of a first threshold (230). As described above, the value of a first threshold may be used to determine if an event has started. In some illustrations, such as the example illustrated in FIG. 2, this is accomplished by changing the value of a flag (e.g., the "EVENT_START" flag of FIG. 2). In such implementations, the value of the flag is set to "1" as long as the value of the total acceleration for a sample is greater than the value of the first threshold. For instance, in the example depicted in FIG. 1B, the value of the flag is set to "1" for all samples between $S_1$ to $S_{16}$ because the respective total acceleration values for these samples exceeds the value of the first threshold.

Although FIG. 2 illustrates the use of an event flag to perform different operations corresponding to the value of the event flag, in other implementations, the computing unit 112 may use any other suitable data processing technique to perform different operations based on the comparisons of the total acceleration and the peak acceleration to the first and second thresholds, respectively.

While the value of the flag is set to "1," the computing unit 112 computes aggregate parameters for the samples that have a total acceleration value that exceeds the value of the first threshold (240). For instance, in the example depicted in FIG. 1B, the computing unit 112 computes aggregate parameters on a sample-by-sample basis for each sample within the group of samples $S_1$ to $S_{16}$. Examples of aggregate parameters (e.g., the event data 156) are described above with respect to FIG. 1B.

In addition, as illustrated in FIG. 2, the aggregate parameters are accumulated as long as the total acceleration value of a sample exceeds the value of the first threshold. For example, after the computing unit 112 completes computing the aggregate parameters for sample $S_1$ from the example in FIG. 1B, the computing unit 112 then executes steps 210, 220, 230, and 240 for the sample $S_2$. This procedure continues for samples $S_3$ to $S_{16}$ and then terminates at step 230 when processing sample $S_{17}$ since the total acceleration value for this sample does not satisfy the predetermined threshold. In this example, the computing unit 110 accumulates the aggregate parameters for samples $S_1$ to $S_{16}$.

If the value of total acceleration for a sample is less than the value of the first threshold in step 230, the computing unit 112 then checks to the value of the flag discussed above. If the value is not equal to "1," then the computing unit 112 reverts back to step 210. Alternatively, if the value of the flag is set to "1," then the computing unit adjusts the value to "0" and then proceeds to step 260.

The computing unit 112 then determines the peak acceleration value from the samples that have been processed while the flag value was equal to "1." For instance, in the example illustrated in FIG. 1B, the computing unit 112 determines the peak acceleration for the samples $S_1$ to $S_{16}$ by selecting the maximum total acceleration value from among the total accelerations calculated for each sample. In this example, the computing unit 112 processed data for the samples $S_1$ to $S_{16}$ in steps 220, 230, and 240, as described above, which the computing unit 112 reaches the step 240 (when the total acceleration for sample $S_{17}$ fails to satisfy the first threshold at step 230).

In some implementations, in addition to measuring the peak acceleration that occurred during a particular time period (e.g., a time period defined by samples included within a detected event), the computing event 112 may determine may also determine an average total acceleration value for an event by averaging the respective total acceleration values within the sampling time period. Alternatively, in other instances, other types of data aggregation techniques may be used to compute different types of aggregate parameters for the sample period.

After determining the peak acceleration, the computing unit 112 then determines if the value of the peak acceleration is greater than the value of the second threshold (260). As described above, the comparison to the second threshold is used to determine if data for a detected event represents motion associated with an athlete's physical activity, representing a significant event, or motion that is associated with noise or other types of insignificant physical activity that is not of interest, representing an insignificant event. In other implementations, the comparison to the second threshold can also be used to determine if the detected event is determined to meet any additional requirements that may be defined as necessary for the data to be worth reporting, e.g., where the significance of the event data is greater than the cost of transmission/reporting to the smart device 120 and the subsequent storage and processing of that event data.

If the value of the peak acceleration does not exceed the value of the second threshold, then the computing unit 112 proceeds to clear the accumulated statistics and reverts back to step 210. For instance, in the example illustrated in FIG. 1B, if the peak acceleration value for samples $S_1$ to $S_{16}$ does not exceed the second threshold, then the computing unit 112 clears the computed aggregate parameters for samples $S_1$ to $S_{16}$, as described above, and proceeds to obtaining sensor data for the sample $S_{17}$ in step 210.

Alternatively, if the value of the peak acceleration does exceed the value of the second threshold, then the computing unit 112 transmits the accumulated data to the smart device 120 (270). For instance, in the example illustrated in FIG. 1B, if the peak acceleration value for samples $S_1$ to $S_{16}$ exceeds the second threshold, then the computing unit 112 transmits the aggregate parameters computed for samples $S_1$ to $S_{16}$, as described above. In this example, this data can represent the event data for the event E1 within the event data 156.

For example, as described previously, the computing unit 112 can transmit the data from the most recently detected event to the smart device 120. In some instances, the transmission can additionally include device-specific instructions on how to display information related to the acceleration measurements. In some implementations, the unit 110 sends the data associated with a particular event to the smart device 120 only at the time or shortly after the time the event terminates. In other implementations, the unit 110 begins sending the data associated with the particular event in real-time as soon as the event starts and completes sending the data at the time or shortly after the time the event terminates. In yet other implementations, the unit 110 additionally or alternatively accumulates the data for multiple events and transmits completed event data to the smart device 120 at a later time that is unrelated to the timing of the events. For example, the unit 110 may transmit the data periodically every 10 minutes, when the unit 110 is shut down, or in response to receiving a particular instruction from a user of the unit 110 by, for example, the user depressing a button or other user interface element on the unit 110.

Figure 3A:
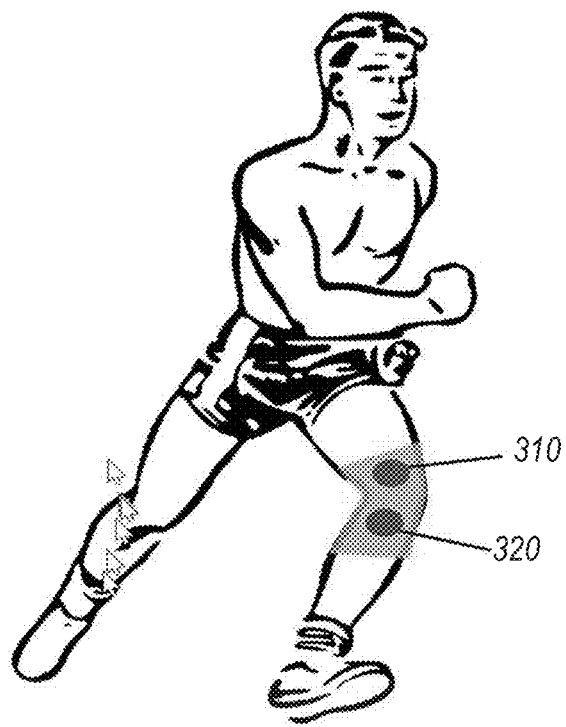
FIGS. 3A and 3B are diagrams that illustrate examples of implementations of an impact measurement system.
Figure 3B:
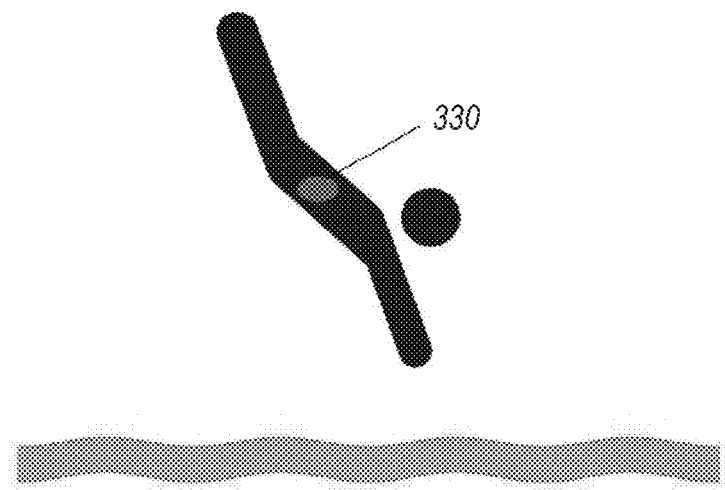

FIGS. 3A and 3B are diagrams that illustrate examples of implementations of a performance measurement system. Referring to FIG. 3A, one implementation of the performance measurement system 100 can include sensors 310 and 320 to perform impact measurements near knee joints. As depicted, the sensors 310 and 320 can be placed in different locations to isolate joints of interest and measure performance data such as differential peak acceleration and differential surge. The impact measurements may indicate knee stress on landing. In addition, multi-appendage analysis or multi-joint analysis can be evaluated or predicted based on differential peak acceleration and differential surge data and cross referenced amongst appendages or joints.

Referring now to FIG. 3B, another implementation of the performance measurement system 100 can include a sensor 330 to perform acceleration, velocity, surge, and/or other motion measurements for a diver entering into the wave during a dive. As depicted, the sensor 330 can be placed on a central location of a diver to quantitatively measure dive execution with respect to surge measurement. For example, a well-executed dive can be determined based on a low surge measurement, whereas a poorly executive dive can be determined based on a high surge measurement. In each of these examples, the sensor 330 may perform measurements prior to dive entry and after dive entry in order to measure the impact between the diver and the water surface.

Although not depicted in FIGS. 3A-3B, in some implementations, the performance measurement system 100 can include sensors that are placed on the waist of a user near the user's center of mass or other specific parts of the body.

Figure 4:
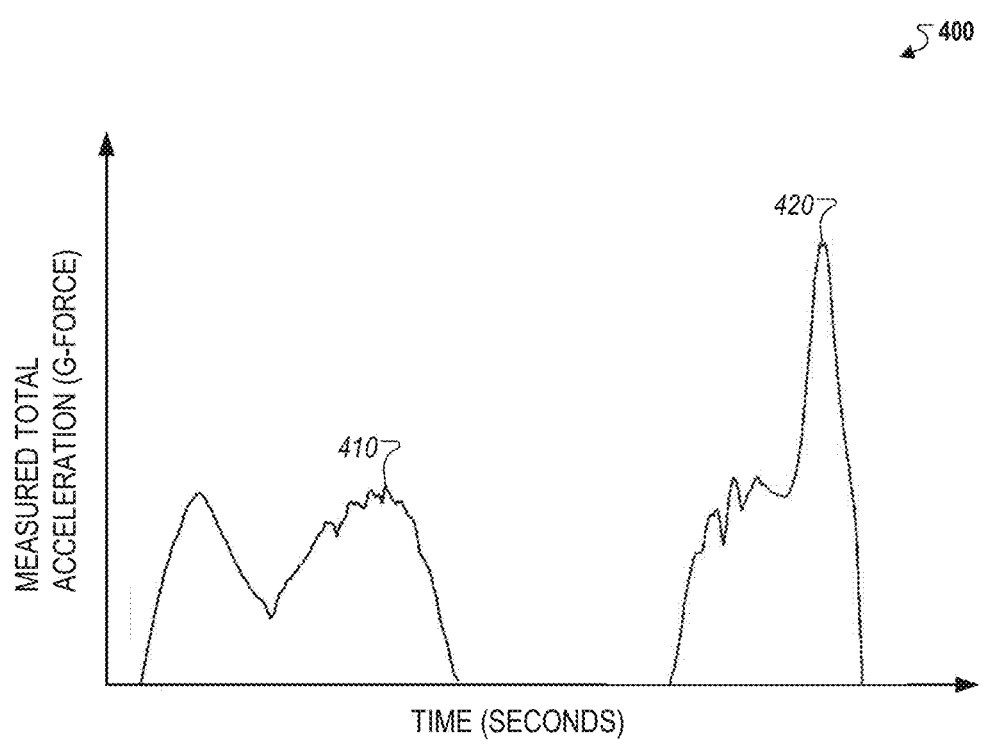
FIG. 4 is a graph that illustrates an example of two events detected by a performance measurement system.

FIG. 4 illustrates a graph 400 depicting measured instantaneous acceleration as a function of time. The graph 400 includes all acceleration measurements that are determined to exceed a specified threshold value. For instance, the graph 400 includes two detected events 410 and 420 with an intervening time period where the measured acceleration did not satisfy the threshold value. In response to determining the occurrence of events 410 and 420, the computing unit 112 of the performance measuring unit 110 computes a set of aggregate parameters for each group as described above in FIG. 1B.

In the two examples illustrated in FIG. 4, the computing unit 112 would report the peak acceleration of the event 420 (e.g., the highest magnitude of measured acceleration during the event) and the correspondingly lower peak acceleration for the event 410. In addition, the computing unit 112 processes event data (e.g., the event data 156) to analyze the rate of change in acceleration over the course of the event (also referred to as "surge" or "jerk"). In the examples illustrated, the event 410 would be reported as having a lower surge value than the event 420, which shows a larger maximum change in acceleration per unit time throughout the event.

The computing unit 112 and/or the smart device 120 can make various inferences based on the difference in surge calculations for the events 410 and 420. For instance, low surge measured during event 410 can indicate that although the athlete was moving during the time period associated with the event, he/she was not undergoing any excessively jerky motion involving abrupt, rapidly evolving physical stress. In comparison, the high surge measured during the event 420 (particularly in the later half) indicates that the athlete may have performed or been subjected to an abrupt, jerky movement, e.g., a poor landing from a jump, an impact with another object or player, or other non-gradual acceleration or deceleration that might be performed intentionally to reach an athletic objective or avoid an obstacle, or perhaps alternatively brought about by fatigue or poor technique. At the extreme, high surge events can be correlated with a change in material properties due to the finite speed of propagation of deformation and vibration, wherein materials can behave as if they were more brittle than they would otherwise be. This phenomenon is used by a martial artist breaking bricks for instance, where the abrupt, rapid transfer of energy from his or her is delivered at a rate that overcomes the brick material's ability to transform the energy into deformation, heat, and sound, so the majority of the applied force goes into fracturing the material. Conversely, athletic pads and vehicle airbags exist to limit the surge experienced by the person that they're meant to protect. The effect also contributes to not just the difference between bending and breaking for rigid materials, but also the difference between stretching and tearing for pliable materials, such as tendons, muscles, and other soft tissues.

The computing unit 112 and/or the smart device 120 can utilize the acceleration measurements for the events 410 and 420 to accomplish various monitoring and/or reporting objectives. For example, because low surge is associated with low-impact physical activity and high surge is associated with high-impact physical activity, the computing unit 112 and/or the smart device may utilize surge measurements to determine events that are likely to place high physical stress on the athlete's body.

The acceleration measurements can additionally be used to differentiate between positive and negative implications of high surge events on the athlete's physical condition. For example, high surge events indicating positive changes in accelerations can be used to indicate explosiveness whereas high surge events indicating negative changes in acceleration can be used to indicate stress, fatigue, and/or the need for technique improvement. In such examples, the performance measuring unit 110 may monitor a current velocity vector to track both magnitude and direction of the athlete's current velocity for the purpose of differentiating between acceleration that increases his or her velocity and acceleration that decreases it.

Various techniques can be used to approximate the surge of an event (or the surge of a portion of an event) while minimizing potential calculation errors due to noise. In some implementations, surge is computed on a sample-by-sample basis by computing the difference between total accelerations of two events and dividing the difference by the sample interval (this is simplest type of the family of discrete derivative approaches known as finite difference approximations). In such implementations, measurement noise may be reduced by applying a low pass filter before and/or after the application of a traditional finite difference approximation technique. In other implementations, surge can be measured by determining the duration of event and then dividing the peak acceleration value by a half of the duration. In such implementations, the surge calculation idealizes an event as a triangle with a base equal to the event duration and a height equal to the peak acceleration measured in that event.

In some implementations, the computing unit 112 and/or the smart device 120 may measure a ratio of the peak acceleration to the average acceleration throughout an event. The average acceleration may be calculated by initially calculating the sum of the total accelerations for each sample throughout the event divided by the number of samples in the event. Two different techniques can be used to compute the sum of the acceleration during an event.

In some implementations, the sum of the acceleration during an event is measured as a cumulative sum of the total acceleration measured for each sample within the event. In such implementations, the total acceleration is determined by applying the Pythagorean theorem in three dimensions to each sample of per-axis acceleration. This produces a single number (also known as a scalar) representing the magnitude of the acceleration described by the per-axis acceleration sample (which is a vector representation). This number is always positive because it represents only how much acceleration is happening, without regard to its direction. This total acceleration is calculated for each sample, and is added to the cumulative sum in an iterative fashion. For instance, because the techniques described are performed in real-time, each time a new sample is processed, the computed total acceleration is added to a cumulative sum that is adjusted during the event. Since the total acceleration is always positive, the cumulative sum grows with every sample. Note that zero-valued total accelerations are also possible, but wouldn't be included in the calculation being described, since they wouldn't be considered as part of an event.

In other implementations, the sum acceleration is measured as a net sum of the per-axis accelerations (not a sum of the magnitude or the absolute value of the acceleration). In such implementations, negatively measured acceleration values along a coordinate direction may cancel out positively measured acceleration values along the same coordinate direction (e.g., −0.1 G measured along the Z-axis cancelling out +0.1 G measured along the Z-axis, or −10 Gs and 3 Gs summing to 7 Gs). For example, a positive measured acceleration value for a sample can be added to a negative measured acceleration value for a following sample include within the event.

The two types of average acceleration that are derived from alternately dividing these two types of sum are referred to as the cumulative average and the net average. These are analogous to the way distance is measured alternately by a vehicle odometer or as the shortest distance between two points (colloquially called "as the crow flies"), respectively.

Figure 5:
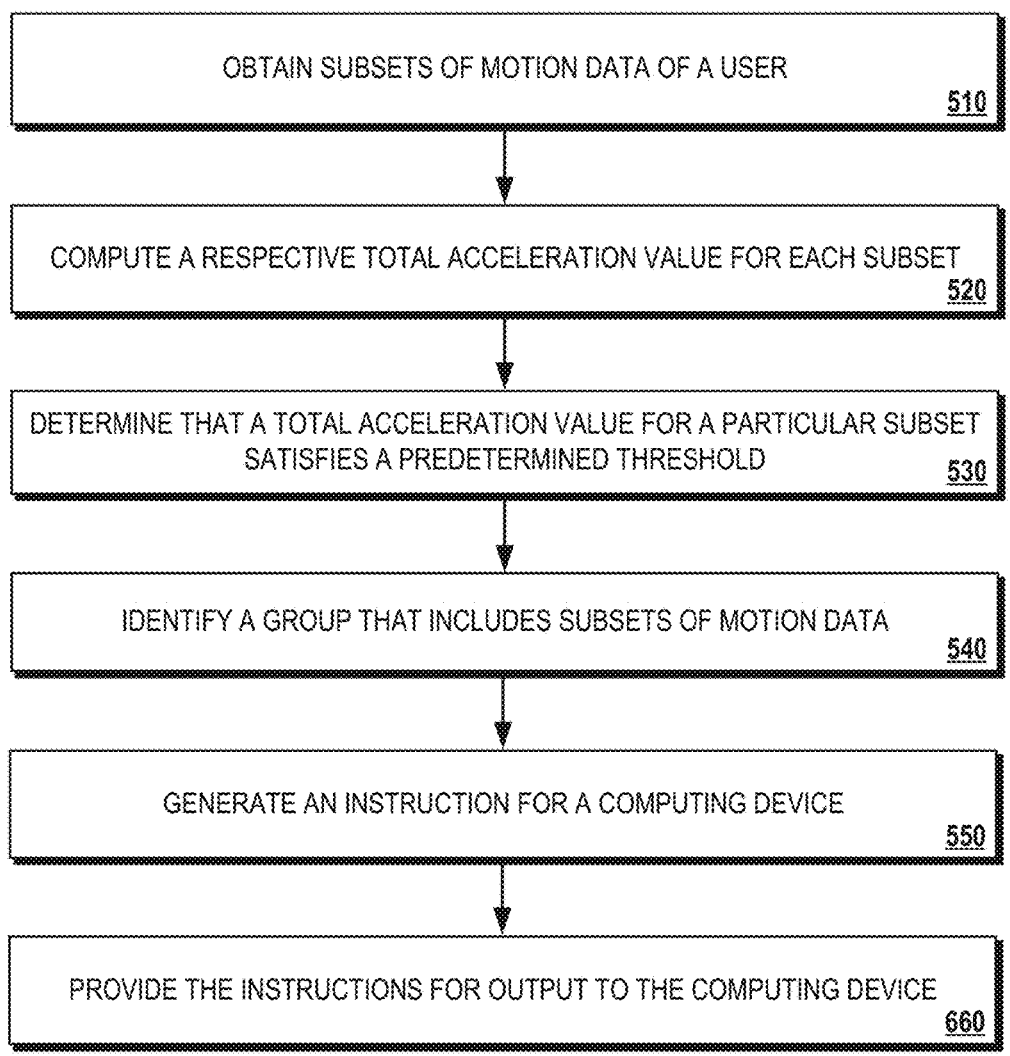
FIG. 5 is a block diagram that illustrates an example of a process for detecting acceleration by an impact measurement system.

FIG. 5 is a block diagram that illustrates an example of a process 500 for measuring impact data. Briefly, the process 500 may include obtaining samples of motion data of a user (510), computing a respective total acceleration value for each sample (520), determining that a total acceleration value for a particular sample satisfies a predetermined threshold (530), identifying a group that includes samples of motion data (540), generating an instruction for a computing device (550), and providing the instructions for output to the computing device (560).

In more detail, the process 500 may include obtaining samples of motion data of a user (510). For instance, the computing unit 112 of the performance measuring device 110 may obtain the raw sensor data 152 from the accelerometer 116a, the gyroscope 116b, and the magnetometer 116c. As described above, the raw sensor data 152 includes multiple samples (or subsets of motion data) that each includes sensor data collected by the accelerometer 116a, the gyroscope 116b, and the magnetometer 116c along each coordinate axis. For example, the sensor data for each sample includes a measured acceleration, a measured direction of movement, and a measured magnetic field along each coordinate axis.

The process 500 may include computing a respective total acceleration value for each sample (520). For instance, the computing unit 112 may compute total accelerations for each sample of motion data that is included within the raw sensor data 152. As described above, total acceleration refers to an aggregate magnitude of instantaneous acceleration measured by the accelerometer 116a. The total acceleration may be computed by using the Pythagorean theorem in three dimensions to combine the measured acceleration along respective coordinate axis (e.g., $A_X$, $A_Y$, and $A_Z$ in FIG. 1B) based on the sensor coordinate system and the relationship between each coordinate axis. The computed total acceleration values for each sample can be stored in the table 154 as illustrated in FIG. 1B, or discarded to conserve memory once information contained in the sample has been used to update the statistics describing the event.

The process 500 may include determining that a total acceleration value for a particular sample satisfies a predetermined threshold (530). For instance, the computing unit 112 may compare the computed total acceleration value of each sample of motion data (e.g., each subset) to a predetermined threshold value such as 1.5 Gs. In some implementations, a total acceleration for a particular sample of motion data satisfies the predetermined threshold if its value exceeds the predetermined threshold value.

The process 500 may include identifying a group that includes samples of motion data (540). For instance, in response to determining that the total acceleration for a particular sample of motion data satisfies the predetermined threshold (e.g., sample $S_1$ in FIG. 1B), the computing unit 112 then identifies a group of subsequent samples of motion data that also satisfy the threshold. As described above, the computing unit 112 iteratively compares each the total acceleration computed for each subsequent sample of motion data after the particular sample to the threshold value until it identifies a subsequent sample that does not satisfy the threshold. For example, as illustrated in FIG. 1B, samples $S_1$ to $S_{16}$ are identified to be in a group because each sample from $S_2$ to $S_{16}$ satisfies the threshold, but sample $S_{17}$ does not satisfy the threshold. In this example, samples $S_2$ to $S_{16}$ represent subsequent samples to sample $S_1$ because they are collected after sample $S_1$.

The process 500 may include generating an instruction for a computing device (550). For instance, the computing unit 112 generates an instruction to the smart device 120 to compute one or more aggregate parameters for a group identified in step 540, and computing one or more athletic performance parameters for the user. Examples of aggregate parameters are described above with respect to FIG. 1B. In addition, examples of athletic performance parameters can include peak acceleration, surge, a predicted amount of kinetic energy expenditure by the user, the power generated by the user, or a predicted physical impact of the detected motion on the user. Each of these athletic performance parameters can be derived based on the raw sensor data of each sample included within the identified group.

The process 500 may include providing the instructions for output to the computing device (560). For instance, as described above in FIG. 1A, the computing unit 112 may transmit the generated instruction to the smart device 120 using any suitable wireless communication protocol.

As described throughout, computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The elements of a computer may include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the systems and techniques described here can be implemented on a computer having a display device (e.g., a CRT (cathode ray tube), LCD (liquid crystal display) monitor, LED (light-emitting diode) or OLED (organic light-emitting diode) monitors) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of implementations have been described. Nevertheless, it will be understood that various modifications may be made without departing from the spirit and scope of the invention. For example, much of this document has been described with respect to messaging and mapping applications, but other forms of graphical applications may also be addressed, such as interactive program guides, web page navigation and zooming, and other such applications.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the claims.

What is claimed is:

1. A computer-implemented method comprising:
   obtaining, from a plurality of sensors, data indicating samples of motion data of a user being contacted by an object;
   computing a respective total acceleration value for each of the samples of motion data;
   determining that a total acceleration value for a particular sample from among the samples of motion data satisfies a predetermined threshold;
   in response to determining that the total acceleration value for the particular sample satisfies the predetermined threshold, identifying a group that includes samples of motion data that (i) are collected after the particular sample, and (ii) are determined to have a particular total acceleration value that satisfies the predetermined threshold;
   generating an instruction to a computing device to (i) compute, for the identified group, one or more aggregate parameters based on the samples of motion data that are included within the identified group, and (ii) compute one or more athletic parameters for the user based at least on the one or more computed aggregate parameters;
   providing the instruction for output to the computing device;
   projecting a movement of the user on a display of the computing device based on the one or more athletic parameters; and
   projecting a movement of the object on the display of the computing device based on the one or more athletic parameters.

2. The method of claim 1, wherein the plurality of sensors comprises at least an accelerometer, a gyroscope, and a magnetometer.

3. The method of claim 2, wherein each sample of motion data includes, for each respective coordinate axis, a measured acceleration, a measured magnetic field direction, and a measured angular velocity.

4. The method of claim 2, wherein computing a total acceleration value for a sample of motion data comprises combining an acceleration measured by the accelerometer, a magnetic field direction measured by the gyroscope, and an angular velocity measured by the magnetometer.

5. The method of claim 1, wherein at least one of the aggregate parameters includes a value of a highest measured total acceleration that is selected from among the measured total accelerations for the samples of motion data included within the identified group.

6. The method of claim 1, wherein the one or more athletic performance parameters comprise a predicted amount of kinetic energy expended by the user during a time period associated with the identified group.

7. The method of claim 1, wherein the one or more athletic performance parameters comprise a predicted physical impact of the detected motion on the user during a time period associated with the identified group.

8. A system comprising:
   one or more processors; and
   one or more computer-readable media including instructions that, when executed by the one or more processors, cause performance of operations comprising:
      obtaining, from a plurality of sensors, data indicating samples of motion data of a user being contacted by an object;
      computing a respective total acceleration value for each of the samples of motion data;
      determining that a total acceleration value for a particular sample from among the samples of motion data satisfies a predetermined threshold;
      in response to determining that the total acceleration value for the particular sample satisfies the predetermined threshold, identifying a group that includes samples of motion data that (i) are collected after the particular sample, and (ii) are determined to have a particular total acceleration value that satisfies the predetermined threshold;
      generating an instruction to a computing device to (i) compute, for the identified group, one or more aggregate parameters based on the samples of motion data that are included within the identified group, and (ii) compute one or more athletic parameters for the user based at least on the one or more computed aggregate parameters;
      providing the instruction for output to the computing device;

projecting a movement of the user on a display of the computing device based on the one or more athletic parameters; and projecting a movement of the object on the display of the computing device based on the one or more athletic parameters.

9. The system of claim 8, wherein the plurality of sensors comprises at least an accelerometer, a gyroscope, and a magnetometer.

10. The system of claim 9, wherein each sample of motion data includes, for each respective coordinate axis, a measured acceleration, a measured magnetic field direction, and a measured angular adjustment.

11. The system of claim 10, wherein computing a total acceleration value for a sample of motion data comprises combining an acceleration measured by the accelerometer, a magnetic field direction measured by the gyroscope, and an angular velocity measured by the magnetometer.

12. The system of claim 8, wherein at least one of the aggregate parameters includes a value of a highest measured total acceleration that is selected from among the measured total accelerations for the samples of motion data included within the identified group.

13. The system of claim 8, wherein the one or more athletic performance parameters comprise a predicted amount of kinetic energy expended by the user during a time period associated with the identified group.

14. The system of claim 8, wherein the one or more athletic performance parameters comprise a predicted physical impact of the detected motion on the user during a time period associated with the identified group.

15. One or more non-transitory computer-readable media having instructions stored thereon that, when executed by one or more processors, causing performance of operations comprising:

obtaining, from a plurality of sensors, data indicating samples of motion data of a user being contacted by an object;

computing a respective total acceleration value for each of the samples of motion data;

determining that a total acceleration value for a particular sample from among the samples of motion data satisfies a predetermined threshold;

in response to determining that the total acceleration value for the particular sample satisfies the predetermined threshold, identifying a group that includes samples of motion data that (i) are collected after the particular sample, and (ii) are determined to have a particular total acceleration value that satisfies the predetermined threshold;

generating an instruction to a computing device to (i) compute, for the identified group, one or more aggregate parameters based on the samples of motion data that are included within the identified group, and (ii) compute one or more athletic parameters for the user based at least on the one or more computed aggregate parameters;

providing the instruction for output to the computing device;

projecting a movement of the user on a display of the computing device based on the one or more athletic parameters; and projecting a movement of the object on the display of the computing device based on the one or more athletic parameters.

16. The one or more non-transitory computer-readable media of claim 15, wherein the plurality of sensors comprises at least an accelerometer, a gyroscope, and a magnetometer.

17. The one or more non-transitory computer-readable media of claim 16, wherein each sample of motion data includes, for each respective coordinate axis, a measured acceleration, a measured magnetic field direction, and a measured angular adjustment.

18. The one or more non-transitory computer-readable media of claim 16, wherein computing a total acceleration value for a sample of motion data comprises combining an acceleration measured by the accelerometer, a magnetic field direction measured by the gyroscope, and an angular velocity measured by the magnetometer.

19. The one or more non-transitory computer-readable media of claim 15, wherein at least one of the aggregate parameters includes a value of a highest measured total acceleration that is selected from among the measured total accelerations for the samples of motion data included within the identified group.

20. The one or more non-transitory computer-readable media of claim 15, wherein the one or more athletic performance parameters comprise a predicted amount of kinetic energy expended by the user during a time period associated with the identified group.

* * * * *